(12) United States Patent
Bullara et al.

(10) Patent No.: US 6,249,965 B1
(45) Date of Patent: *Jun. 26, 2001

(54) METHODS FOR MAKING SMALL-DIAMETER IRIDIUM ELECTRODES

(75) Inventors: Leo A. Bullara, Glendora; Douglas B. McCreery, Pasadena, both of CA (US)

(73) Assignee: Huntington Medical Research Institutes, Pasadena, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/173,577

(22) Filed: Oct. 15, 1998

Related U.S. Application Data

(60) Provisional application No. 60/062,126, filed on Oct. 15, 1997.

(51) Int. Cl.[7] .............................. H01R 43/16; A61B 5/04
(52) U.S. Cl. .............................. 29/874; 600/377; 600/378
(58) Field of Search ....................... 29/868, 874; 385/35, 385/123, 128; 128/639, 635; 204/27, 29, 83; 600/377, 378

(56) References Cited

U.S. PATENT DOCUMENTS

| | | | | |
|---|---|---|---|---|
| 3,826,244 | * | 7/1974 | Salcman et al. | 128/2.1 E X |
| 4,959,130 | * | 9/1990 | Josowicz et al. | 204/32.1 |
| 5,152,877 | * | 10/1992 | Nishino et al. | 204/129.4 |
| 5,269,890 | * | 12/1993 | Marchtwka | 204/146 |
| 5,378,343 | * | 1/1995 | Kounaves et al. | 204/413 X |
| 5,630,932 | * | 5/1997 | Lindsay et al. | 205/645 X |
| 5,664,036 | * | 9/1997 | Islam | 385/31 |

* cited by examiner

*Primary Examiner*—Jessica J. Harrison
*Assistant Examiner*—Binh-An Nguyen
(74) *Attorney, Agent, or Firm*—Christie, Parker & Hale, LLP

(57) ABSTRACT

Iridium electrodes of very small diameter such as 35 microns are formed from larger-diameter commercially available iridium wire by an electrolytic etching process. A saturated solution of sodium chloride in a preferred etching solution. The electrodes are formed with sharp conical tips which can be rounded or blunted if desired by additional etching. Platinum lead wire is welded to the electrode shank, and the electrode is coated with an insulating varnish which is ablated at the electrode tip to expose a conductive surface.

5 Claims, 5 Drawing Sheets

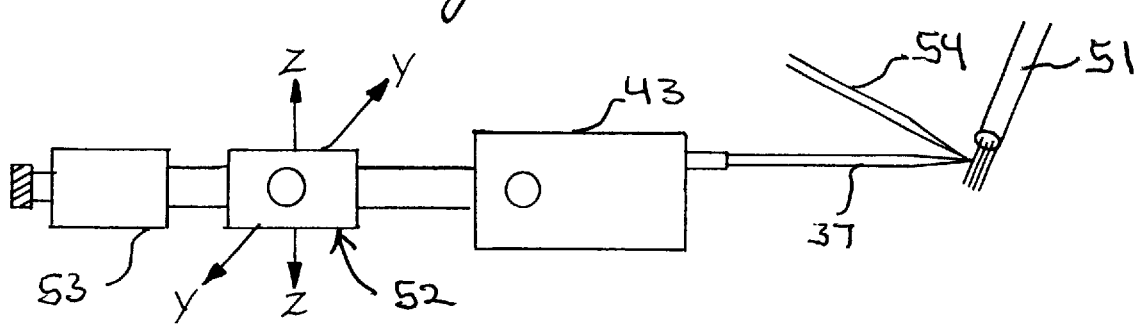

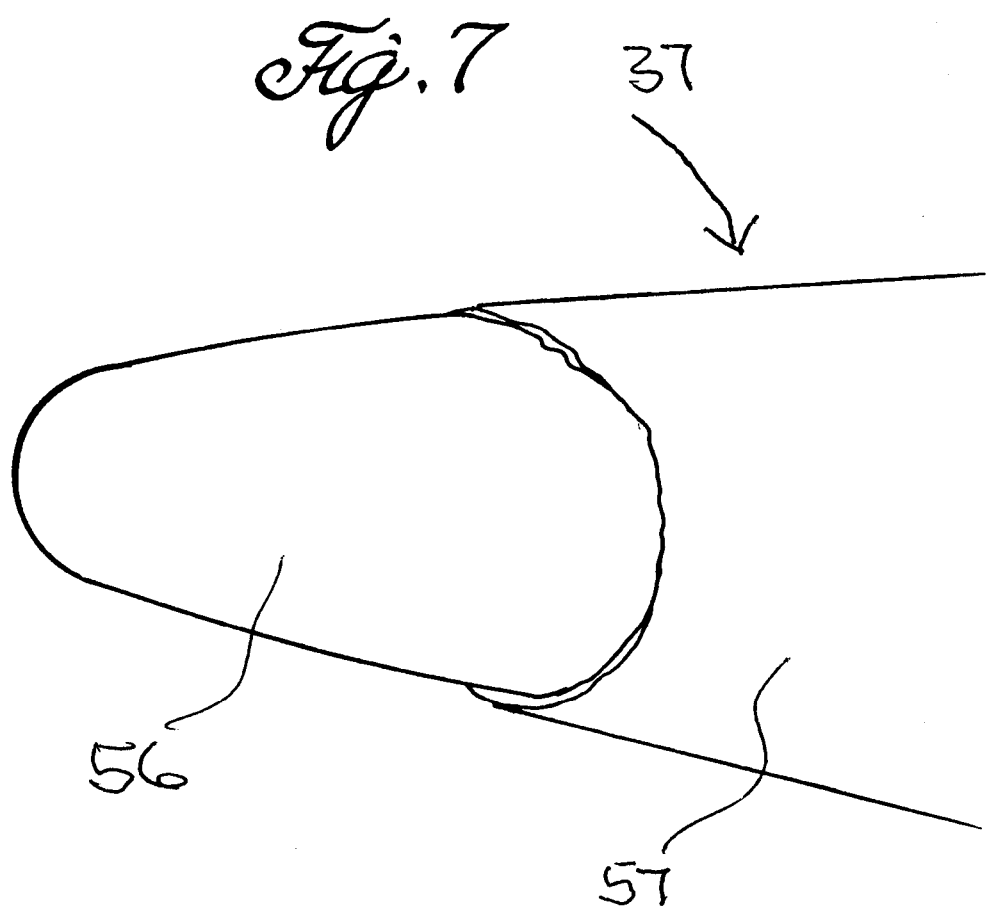

METHODS FOR MAKING SMALL-DIAMETER IRIDIUM ELECTRODES

CROSS REFERENCE TO RELATED APPLICATION

This application claims the benefit of U.S. Provisional Application No. 60/062,126 filed Oct. 15, 1997.

BACKGROUND OF THE INVENTION

This invention relates to methods and apparatus for making small-diameter iridium electrodes useful for electrical stimulation of nerves in the central or peripheral nervous systems of animals and humans. Tiny electrodes of this type are especially useful for electrical stimulation of selected regions of the cerebral cortex, and are in some applications arranged in arrays of many (e.g., 10 to as many as 50 or more) closely spaced and centrally supported electrodes.

Iridium is an excellent material for such electrodes due to its stiffness, biocompatibility, low capacitance (as compared to platinum), and acceptance of surface oxidation which prevents long-term erosion after implantation. Small-diameter iridium wire which was formerly commercially available (and believed to have been made by delicate drawing of the wire through dies of decreasing diameter) is no longer produced in diameters smaller than about 125 microns, but the need for smaller diameters continues in the field of nerve-stimulating electrodes.

The techniques of this invention have been used to produce pin-like electrodes with shaft diameters in the general range of 10-to-50 microns, and with tapered or sharpened tips with diameters as small as 1-to-2 microns. These techniques are also useful in controlled blunting of the sharpened tips, polishing of the etched electrodes, and in the application of an insulating coating to regions of the electrode shaft which are not to be in electrical contact with tissue in which the shaft is inserted.

DESCRIPTION OF THE DRAWINGS

FIG. 6 is a schematic view of a laser ablation system for removing insulation from a tip of the electrode; and FIG. 7 is a perspective view of an electrode tip after ablative removal of insulation.

SUMMARY OF THE INVENTION

Commercially available iridium wire of about 125-micron diameter is electrolytically etched at optimal current levels in a saturated solution of sodium chloride to achieve diameter reduction to 35 microns or less. Further etching steps form a tapered end on a segment of the wire forming an electrode, and the sharp tip can be rounded or blunted if desired. Lead wire is welded to the electrode, and an insulating film is formed on the electrode surface except for a small exposed and conductive tip.

DESCRIPTION OF THE PREFERRED EMBODIMENTS

Figure 1:
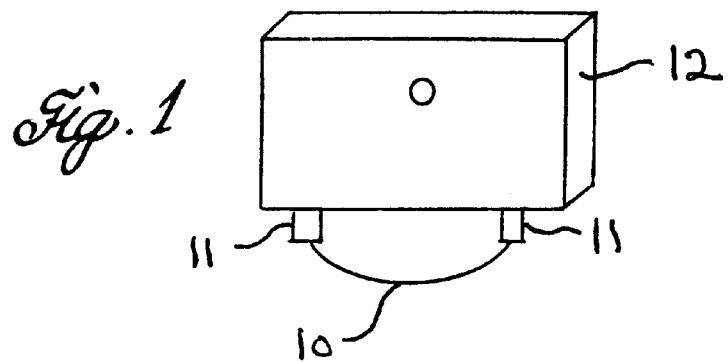
FIG. 1 is a perspective view of a brass block holding an iridium wire.

A first step in the diameter reduction by electrolytic etching of commercially available iridium wire of about 125-micron diameter is to solder the ends of a length (typically about 4-to-6 cm) of a wire 10 to a pair of pin-type connectors 11 (Amphenol Model 220-P02-100 connectors are suitable) as shown in FIG. 1. Prior to soldering, the wire is cleaned by sonicating in acetone, followed by air drying. After soldering to the connectors, flux is removed from the soldered junctions by sonicating in detergent (a commercially available "Micro" product is suitable), followed by detergent-residue removal by three 30-second periods of sonification in distilled water. The wire is then formed in the approximate shape of a catenary as shown in FIG. 1, and mounted on a brass block 12 by plugging connectors 11 into sockets formed in the block.

Figure 2:
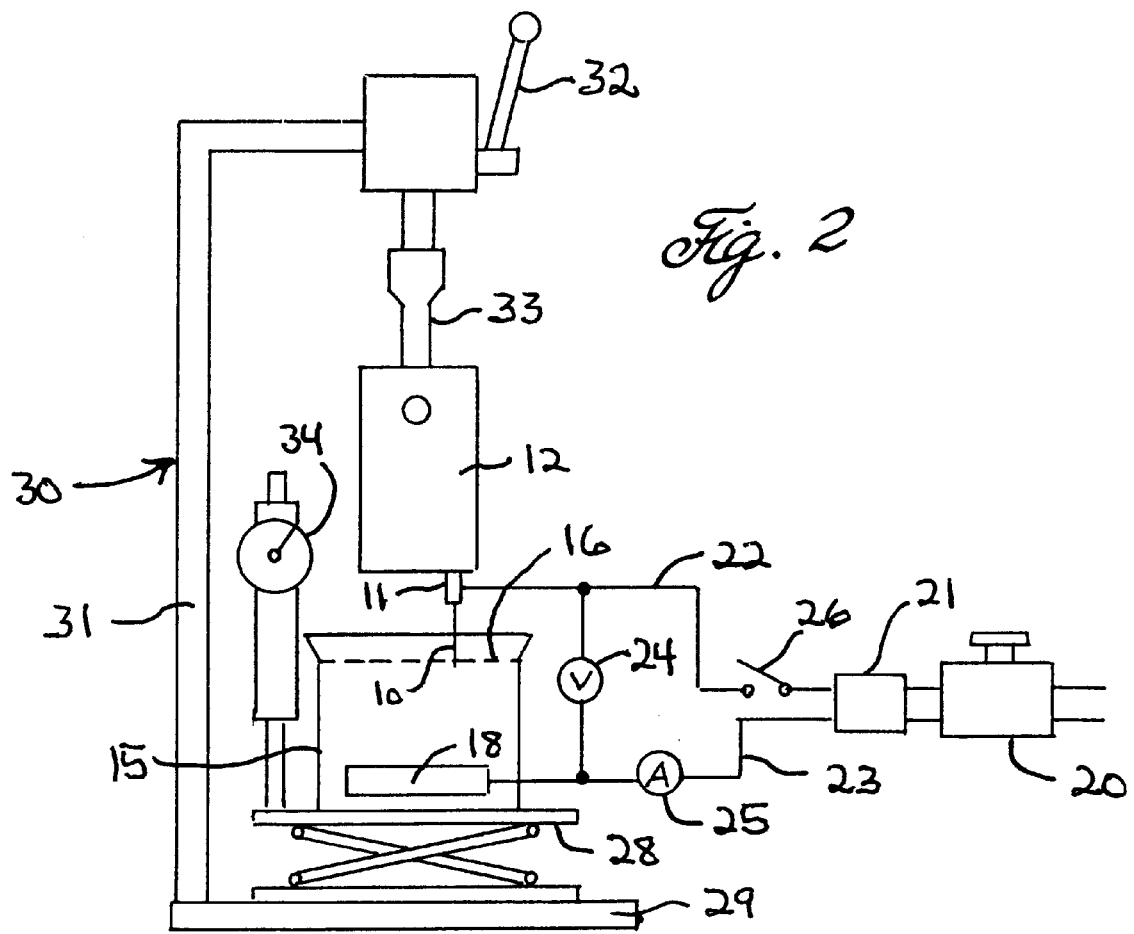
FIG. 2 is a schematic side elevation of electrical and mechanical components used for etching of the wire.

Block 12 is then supported above a tank 15 containing an etching solution 16 which is preferably a saturated solution of sodium chloride (an environmentally safe and nontoxic material) as shown schematically in FIG. 2. The block is then lowered to just above the surface of solution 16 so entire length of wire 10 is immersed in the solution.

A carbon-block electrode 18 is positioned at the bottom of tank 15, and is connected to an external circuit as shown in FIG. 2. The circuit includes a variable transformer 20 (the Variac type is suitable) connected to a stepdown transformer 21. One output lead 22 from transformer 21 is connected to connector 11 or block 12, and a second output lead 23 is connected to carbon electrode 18. A voltmeter 24 monitors output voltage of transformer 21 as applied between the brass and carbon blocks, and a series-connected ammeter 25 is connected in lead 23. A series-connected switch 26 in lead 22 enables initiation and termination of etching cycles.

Tank 15 is supported on a precision scissors jack 28 which in turn rests on a base 29 of a drill press-like stand 30. The stand has an upright frame 31 extending from base 29 to an elevation adjusting arm 32 for varying the vertical positioning of a chuck or clamp 33 secured to block 12. Vertical positioning of the top of scissors jack 28 (and hence of tank 15) is displayed on a precision dial indicator 34.

An important feature of the invention is the finding that an optimum 60-cycle alternating current of about 95 to 110 milliamperes per square millimeter and preferably about 106 milliamperes per square millimeter of iridium-wire surface results in a smooth etched wire surface with minimum etching time. For example, when etching a 6-cm length of wire having an initial diameter of 125 microns, optimum current level is easily calculated by the following equation:

$$\frac{106\,\text{ma}}{\text{mm}^2} \times \pi \times \text{diameter} \times \text{length} =$$

$$\frac{106\,\text{ma}}{\text{mm}^2} \times \pi \times 0.125\,\text{mm} \times 60\,\text{mm} = 2.5\ \text{amperes}$$

Because the surface area of the wire diminishes as etching progresses, etching is done in stages or cycles of decreased current flow. During initial setup, the diameter of the wire is monitored microscopically at intervals of 10 or 15 minutes, and the current appropriately decreased according to the above formula. As experience is gained, diameter monitoring becomes unnecessary, and an etching protocol as shown below (and which is based on an initial diameter of 125 microns) can be established for a desired final diameter of say 35 microns.

| Etching stage | Current (amperes) | Etching Time (minutes) | Initial Diameter (microns) | Final Diameter (microns) |
| --- | --- | --- | --- | --- |
| 1 | 2.5 | 10 | 125 | 103 |
| 2 | 2.0 | 20 | 103 | 53 |
| 3 | 1.1 | 5 | 53 | 40 |
| 4 | 1.1 | 2 | 40 | 35 |

As suggested by this tabulation, close control of current density is of primary importance in the relatively long-term etching during the first three stages. When etching is complete, any residual sodium chloride is removed by sonication with distilled water.

The etched and cleaned iridium wire is then carefully cut into segments of about one centimeter (depending on the desired length of the final electrode) in length. Each segment is then seated in another pin-type connector 11 as already described, and soldered in place. The cleaning procedure described above is performed after completion of soldering.

The next step is to form a conical taper on the free end of the iridium wire segment. Supporting connector 11 is secured to a brass block of generally the same style as block 12, and which is again mounted in stand 30 as shown in FIG. 2 to position the wire tip just above the surface of etching solution 16. The precision scissors jack is then slowly elevated until the very end of the wire tip contacts solution 16 as signaled by an indication on ammeter 25 of a small current flow. Switch 26 is then opened, and dial indicator 34 is zeroed.

The scissors jack is then elevated about 350 microns to immerse the lower end of the wire in the etching solution, and switch 26 is closed to apply about 20 volts across the wire and carbon electrode 18. Etching is continued until current flow drops to zero, indicting that the lower end of the wire has been etched away. The purpose of this step is to eliminate residual stress in the wire as caused by cutting the wire into segments.

With clamp 33 stopped against further downward travel (but free to be raised by arm 32), the precision scissors jack is again elevated to immerse about 350 microns of the lower end of the wire in the etching solution. Switch 26 is closed to apply a potential of about 20 volts between the wire and electrode 18, and the wire lower end is dipped in and out of the etching solution by raising and lowering clamp 33 for about 7 seconds at a rate of 4 dips per second. Microscopic inspection will show that the lower end is now conically shaped (the core typically has an included angle of about 7 degrees) with a sharp tip.

In some applications, it is desirable to round the tip of the conical wire end. This is easily done while the brass block and wire are still mounted on stand 30. A potential of about 12 volts is applied between the wire and electrode 18, and about 100 microns of the sharp lower end of the wire is immersed in the etching solution. Switch 26 is then activated through ten on-off cycles of one second on and one second off. This procedure will round the end of the conical tip to a radius of curvature of about 2 microns.

Figure 3:
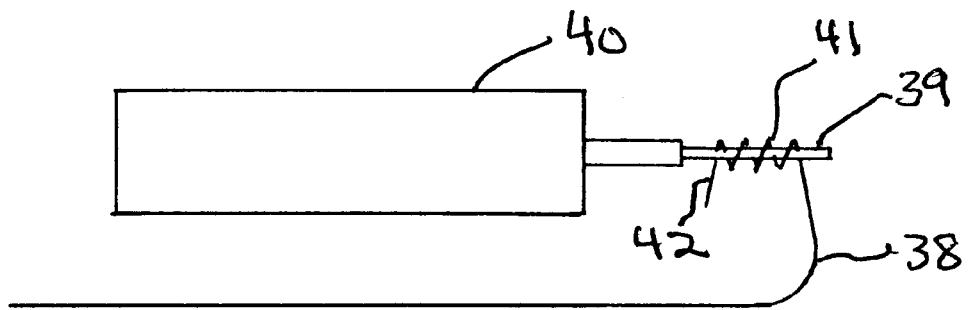
FIG. 3 is a side view of a holder and mandrel for coiling a lead wire.
Figure 4:
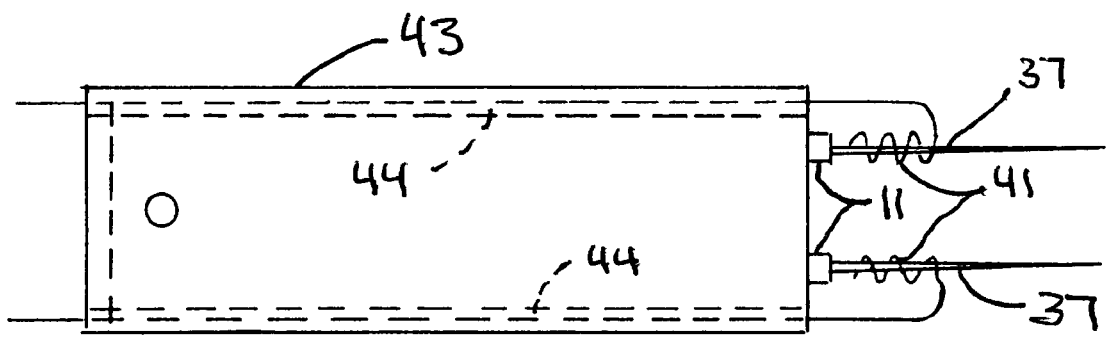
FIG. 4 is a top view of a block holding a pair of etched iridium electrodes with coiled lead wires fitted thereover.

The next step is to weld a platinum lead wire to a now formed and conically tipped electrode 37 (FIG. 4). Preferably, commercially available pure platinum wire of 0.002-inch diameter is used for the lead wire. Referring to FIG. 3, a deinsulated end of such lead wire 38 is coiled around a mandrel 39 having a diameter (e.g., 35 microns) corresponding to the shank diameter of the electrode. The shank of mandrel 39 is secured to a brass block 40 for ease of handling. When a lead-wire coil 41 is so formed, a protruding end 42 is snipped off.

Figure 5:
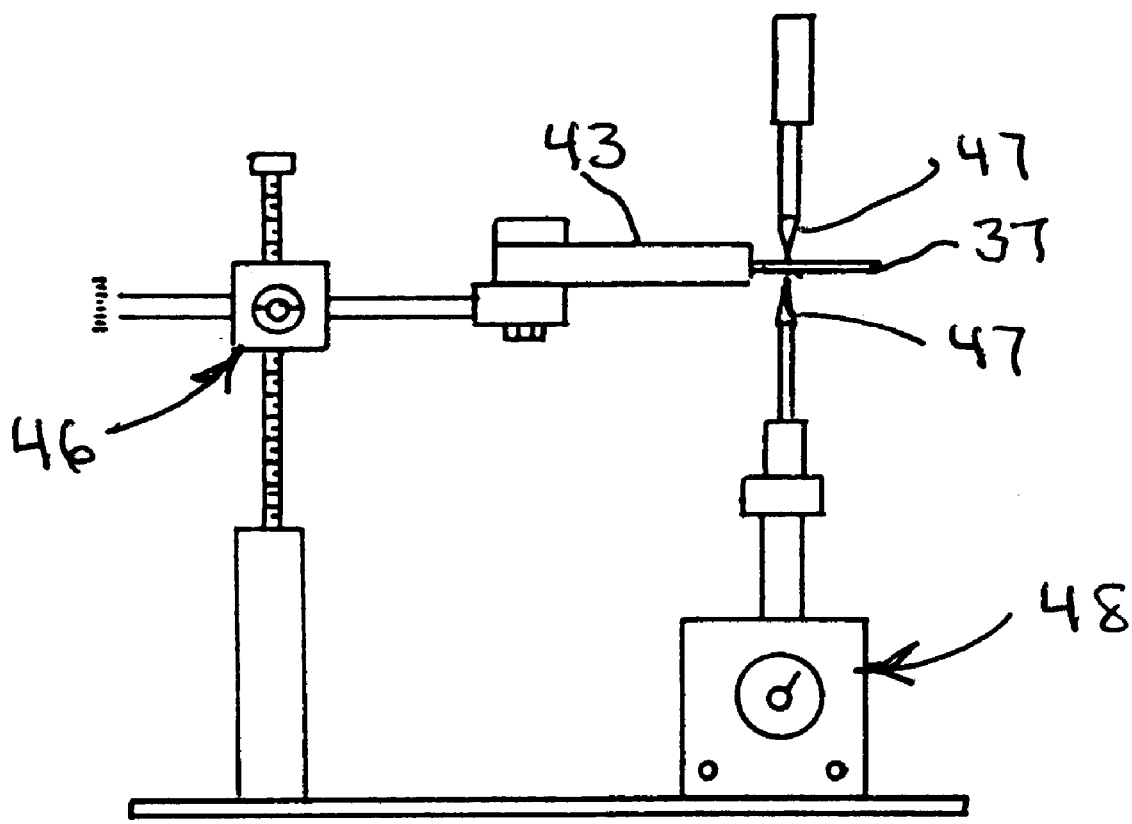
FIG. 5 is a schematic side elevation of components used to weld the lead wire to the electrode.

Referring to FIG. 4, electrode 37 and connector 11 are clamped in a brass holding block 43, and preferably two electrodes are so mounted as shown in the drawing. Grooves 44 are formed in opposite side edges of the block to receive the free end of each lead wire. Lead-wire coils 41 are then slipped over the electrode shank. The block is then secured to a micromanipulator 46 as shown in FIG. 5, and the electrode and coil positioned between welding tips 47 of a precision spot welder 48.

The welding tips are over the approximate center of coil 41, and the welder is actuated at about 2.4 watt-seconds with a tip pressure of about 0.25 kilograms. After welding, the unwelded end of the coil is cut and removed, and the weld junction is sonicated in detergent (Micro) for about one minute to remove weld residue, followed by three 30-second cycles of deionized-water sonification to remove any residual detergent.

Most applications require insulation of the electrode shank so only the end of the conical electrode tip is conductive. the electrodes remain seated on block 43, and a high-temperature baking varnish (Epoxylite 6001-50 is suitable) is placed in a sonicating bath. The electrodes are then immersed in the agitated varnish, and slowly withdrawn during sonication to prevent formation of varnish bubbles.

The coated electrodes are then placed in a vacuum oven which is evacuated to −84 kPa, and maintained at that low pressure for degassing for about 15 minutes, followed by slowly increasing the pressure to ambient. The electrodes are then placed in an oven which is initially heated to about 110° C. for 30 minutes for further degassing, with temperature thereafter increased to 165° C. for another 30 minutes for baking of the varnish film.

Because the resulting insulating film is very thin, the coating procedure is repeated two times. The second coating cycle is identical to the first as already described, and the third cycle differs only in that sonification is terminated as the electrodes are withdrawn, and the resulting thicker coating is based at 165° C. for 60 minutes instead of 30 minutes.

Because the tips as well as the shanks of the electrodes are now varnish coated, it is necessary to deinsulate the tips, and this is most conveniently done by laser ablation. An ErYAG laser 51 of 2.97 micron wave length is suitable (and available from Premier Laser Company), and the equipment setup is shown in FIG. 6. Electrode 37 as still mounted on block 43 is secured to a three-axis stereotaxic micromanipulator 52 with a precision X-axis depth micrometer 53. A stainless-steel shield 54 covers the electrode except for the tip to be ablated.

The laser is then set at an energy level of 50 mJ, and a pulse rate of 10 pps. The laser is actuated for 5 seconds, and then the electrode is rotated 180 degrees so the back surface can be similarly ablated. Preferably, the laser ablation is performed in a helium environment.

FIG. 7 illustrates a now-deinsulated rounded conical tip 56 of electrode 37, with insulation 57 remaining on the remainder of the electrode. The now-completed electrodes can be used individually, or in arrays, and can also be activated by forming a layer of iridium oxide on the uninsulated tip.

What is claimed is:

1. A method for reducing the diameter of iridium wire to less than about 50 microns for making neurological electrodes, comprising the step of electrolytically etching the wire in a saturated solution of sodium chloride by an electrical current flowing through the solution and wire.

2. The method defined in claim 1 in which the electrical current is in the range of 95 to 110 milliamperes per square centimeter of wire exposed to the etching solution.

3. The method defined in claim 1 in which the electrical current is about 106 milliamperes per-square centimeter of wire exposed to the etching solution.

4. The method defined in claim 2 in which an end of the wire is further etched to form a conically tapered tip.

5. The method defined in claim 4, and further comprising the step of coating an insulating film on the etched wire, and removing the film from an end of the tapered tip by laser ablation.

* * * * *